United States Patent [19]

Cooper et al.

[11] 4,242,359

[45] Dec. 30, 1980

[54] SPERMICIDAL AGENTS

[75] Inventors: George W. Cooper, New York, N.Y.; Ronald J. Young, Stamford, Conn.

[73] Assignee: Cornell Research Foundation, Inc., Ithaca, N.Y.

[21] Appl. No.: 968,332

[22] Filed: Dec. 11, 1978

Related U.S. Application Data

[63] Continuation-in-part of Ser. No. 783,622, Apr. 1, 1977, abandoned.

[51] Int. Cl.³ .............................................. A61K 31/13
[52] U.S. Cl. .................................... 424/325; 424/267; 424/320; 424/330; 424/DIG. 14
[58] Field of Search ................ 424/325, 330, DIG. 14

[56] References Cited

U.S. PATENT DOCUMENTS

| | | | |
|---|---|---|---|
| 2,361,524 | 10/1944 | Allardt | 424/325 X |
| 2,464,284 | 3/1949 | Alles | 424/325 |
| 2,742,397 | 4/1956 | Ott | 424/325 |
| 3,143,463 | 8/1964 | Holm et al. | 424/325 |
| 3,227,756 | 1/1966 | Richter et al. | 424/330 |
| 3,376,196 | 4/1968 | Dunn | 424/325 |
| 3,981,677 | 9/1976 | Halasz et al. | 8/10.2 |
| 4,018,818 | 4/1977 | Yamamoto et al. | 424/330 X |
| 4,038,418 | 7/1977 | Möller et al. | 424/325 X |

OTHER PUBLICATIONS

Chemical Abstracts 70:86091h (1969)
Chemical Abstracts 70:65542t (1969)

*Primary Examiner*—Leonard Schenkman
*Attorney, Agent, or Firm*—Schwartz, Jeffery, Schwaab, Mack, Blumenthal & Koch

[57] ABSTRACT

Disclosed is a method for treating mammalian spermatozoa with amphipathic amines in order to induce loss of fertility and/or head-tail cleavage of the sperms under mild physiological conditions. In the presence of primary alkyl or cycloalkyl amines containing between 4 to 7 carbon atoms at concentrations of about 15 λ/ml, sperms are rapidly dissociated into heads and tails under physiological pH- and temperature-conditions. Further disclosed are topical contraceptive compositions containing amphipathic amines.

11 Claims, No Drawings

SPERMICIDAL AGENTS

This invention was made in the course of work under a grant or award from the Department of Health, Education and Welfare, National Institute of Child Health and Human Development, and the Rockefeller Foundation.

The present application is a continuation-in-part application of application Ser. No. 783,622, filed on Apr. 1, 1977, now abandoned.

BACKGROUND OF THE INVENTION

The present invention relates to spermicidal agents and their use in biochemical analysis and in birth-control.

Despite the recent growth of research in mammalian reproductive biology, biochemical analysis of the spermatozoa has progressed relatively slowly, due to the lack of simple and satisfactorily mild agents and/or procedures for subcellular fragmentation, especially for head-tail cleavage in the sperm. In the past, head and tail separation was possible only under extreme conditions of change in pH, sonication (treatment with high frequency sound waves), digestion with enzymes, etc. Until now, chemically induced head-tail cleavage has been accompanied by varying degrees of structural damage to the subcellular organelles.

Conventional topical contraceptive compositions are not very satisfactory. Since the pharmacologically active agents which are known so far to destroy the spermatozoa also tend to detrimentally affect and irritate the vaginal mucosa, these agents cannot safely be applied in spermacidal amounts.

SUMMARY OF THE INVENTION

It is an object of the present invention to provide readily available spermicidal agents and/or compositions.

It is a further object of the present invention to provide such agents and/or compositions which are effective under mild and/or physiological conditions.

It is a further object of the present invention to provide a simple and mild method for rapidly killing mammalian spermatozoa.

It is yet a further object of the present invention to provide such a method which permits the killing and/or loss of fertility of mammalian spermatozoa at physiological conditions.

It is still a further object of the present invention to provide such a method which permits the dissociation of spermatozoa into heads and tails with minimal damage to the structure of the subcellular organelles, and is suited for biochemical analysis purposes.

It is still a further object of the present invention to provide non-toxic topical contraceptive compositions which exhibit a high contraceptive activity without being irritating to the vaginal mucosa.

It is still a further object of the present invention to provide a method for preventing pregnancy in female mammals.

In order to accomplish the foregoing objects according to the present invention, there is provided a method for killing mammalian spermatozoa, which comprises contacting mammalian spermatozoa with a spermicidally effective amount of an amphiphathic* primary or secondary organic amine or an amphipathic organic tertiary diamine.

*amphipathic compounds are compounds containing polar and hydrophobic groups

Suitable amphipathic amines are primary or secondary amines wherein the nitrogen is substituted by unbranched, branched or cyclic aliphatic alkyl groups which are unsubstituted or substituted by alkenyl-, alkinyl-, or aryl-groups, or is part of a non-aromatic heterocyclus. These amines may comprise monocyclic and oligocyclic compounds. The total number of carbon atoms within the amines may be between 1 and about 50, preferably between 2 and about 25, carbon atoms. The aryl groups may be mono-, bi-, or tricyclic and may be carbocyclic or contain 1 or 2 hetero atoms. Examples of carbocyclic aryl groups are phenyl, tolyl, naphthyl, biphenyl or anthracenyl. Examples of heterocyclic aryl groups are pyridyl, indolyl, phenothiazyl, etc. The non-aromatic heterocyclus may be saturated or unsaturated and may contain a second hetero atom. Examples are morpholine, piperazine, pyrroline, pyrrolidine, piperidine or tetrahydrochinoline. The amines may be further substituted by at least one substituent selected from the group consisting of amino, lower mono- or dialkylamino, hydroxy, lower alkoxy, mercapto, lower alkylthio, carboxyl, lower alkoxycarbonyl and halogen. Preferably, any such additional substituent is a polar group able to accept a proton, e.g., an amino group or else a sulfur-containing group.

Thus, the amphipathic primary or secondary amines which are used in the methods and compositions according to the present invention are amines of the formula I

wherein $R_1$ represents hydrogen, an alkyl-, cyclic alkylalkenylalkyl-, or alkinylalkyl group, a carbocyclic arylalkyl group, or a heterocyclic arylalkyl group containing 1-2 hetero atoms, which groups are unsubstituted or substituted by at least one substituent selected from the group consisting of amino, lower mono- or dialkyl amino, hydroxy, lower alkoxy, mercapto, lower alkylthio, carboxyl, lower alkoxycarbonyl, and halogen;

$R_2$ represents an alkyl-, cyclic alkyl-, alkenylalkyl-, or alkinylalkyl group, a carboxylic arylalkyl group or a heterocyclic group containing 1-2 hetero atoms, which groups are unsubstituted or substituted by at least one substituent selected from the group consisting of amino, lower mono- or dialkyl amino, hydroxy, lower alkoxy, mercapto, lower alkylthio, carboxyl, lower alkoxycarbonyl, and halogen;

or $R_1$ and $R_2$ together with the nitrogen atom form a non-aromatic heterocyclus containing 1 to 2 hetero atoms; which is unsubstituted or substituted by at least one substituent selected from the group consisting of amino, lower mono- or dialkyl amino, hydroxy, lower alkoxy, mercapto, lower alkylthio, carboxyl, lower alkoxycarbonyl and halogen.

Suitable tertiary diamines are tetra (lower) alkyl (lower) alkylene diamines.

It has been found that when an amphipathic primary or secondary amine or an amphipathic tertiary diamine is added to a spermatozoa-containing medium, this amine has an immediate spermicidal effect. Sperm-motility ceases and there are multiple changes in morphology of the plasma and/or acrosomal membranes, as viewed at the ultrastructural level with the electron microscope.

The amphipathic amines are spermacidally effective in water-containing media in relatively low concentrations and under very mild reaction conditions, e.g., at normal temperatures, for instance, temperatures between about 30 and about 40° C., and at physiological pH values which are normally found in the natural environment of the sperm, e.g., at pH values between about 4 and about 9.

Because of the mild conditions under which the amphipathic amines can be applied, they are especially useful in biochemical analysis for fragmentating spermatozoa without doing much structural damage to subcellular organelles. For example, mammalian spermatozoa are dissociated into heads and tails with minimal damage to the structures of either heads or tails by primary amines containing 4 to 6 carbon atoms in concentrations as low as about 15 lambda (1 lambda = $10^{-6}$ liters) per ml in suitable buffer solutions at pH-values of between about 7 and about 9.

The ability of the amphipathic amines to attack mammalian spermatozoa under physiological conditions and in low concentrations renders them equally useful in birth-control as contraceptive agents.

Preferred are amphipathic amines which exhibit a dissociation constant, pKa, in aqueous solutions of such a magnitude that at least a portion of the amine is present in effective form at physiological pH-values, e.g., at pH-values between about 4 and about 9, particularly between about 4.5 and about 8. Amines which exhibit a pKa of between about 8 and about 12, particularly between about 9 and about 12, preferably between about 9 to about 10, are especially suited.

It is advisable to limit the molecular weight of the amine molecule so that the molecular size of the amine does not inhibit its passing the cellular membrane of the mammalian spermatozoa. Suitable molecular weights are between about 30 and about 600, preferably between about 70 and about 300.

Especially suited are amines of the formula (I) wherein $R_1$ is hydrogen or lower alkyl, e.g., alkyl containing 1 to 4 carbon atoms, and $R_2$ contains from about 2 to 20 carbon atoms and represents alkyl, alkenyl, cycloalkyl, alkyl (preferably lower alkyl) substituted cycloalkyl, cycloalkylalkyl, alkyl (preferably lower alkyl) substituted cycloalkylalkyl, phenylalkyl, or alkyl (preferably lower alkyl) substituted phenylalkyl, or $R_1$ and $R_2$ together form an alkylene or alkenylene group containing 2 to 6 carbon atoms or a $CH_2$—$CH_2$—X—$CH_2$—$CH_2$-group, wherein X is oxygen, sulfur or lower alkyl amino.

In this specially suited group of amines also the hydrocarbon-substituents $R_1$ and $R_2$ may be unsubstituted or substituted by at least one substituent selected from the group consisting of amino, lower mono- or dialkyl amino, hydroxy, lower alkoxy, mercapto, lower alkylthio, carboxyl, lower alkoxycarbonyl and halogen. Preferably, the hydrocarbon groups $R_1$ and $R_2$ are unsubstituted or substituted by amino, mono lower alkyl amino, hydroxy or lower alkoxy.

Especially suitable amphipathic tertiary diamines are diamines of formula II

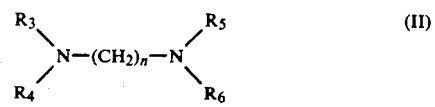

wherein
n is a number from 2–4, and
$R_3$, $R_4$, $R_5$, and $R_6$ each represent lower alkyl, e.g., alkyl containing 1–5 carbon atoms, preferably methyl.

Examples of suitable amines of formula (I) are ethylmethylamines, dipropylamines, propylamines, butylamines, octadecylamines, allylamine, oleylamine, cyclopropylamine, cyclohexylamine, cyclopropylmethylamine, p-methylcyclohexylamine, methylcyclobutylmethylamine, benzylamine, p-tolylmethylamine, 4-phenylbutylamine, morpholine, thimorpholine, N-methylpiperazine, piperidine, tetrahydropyridine, pyrrolidine, pyrroline, propyleneamine, or ethyleneamine.

Particularly suited amines of formula (I) are amines wherein $R_1$ is hydrogen and $R_2$ is an alkyl group, which may be straight or branched, and preferably is a primary alkyl group containing 3 to 24, preferably 3 to 7 carbon atoms, or a cycloalkylalkyl or cycloalkyl group containing 3 to 7 carbon atoms. Examples of such preferred amines are n-propylamine, n-butylamine, isobutylamine, n-heptylamine, cyclohexylamine, or cyclopropylmethylamine.

An especially preferred group of amphipathic amines comprises
amines of formula I, wherein
$R_1$ is hydrogen or alkyl containing 1–7 carbon atoms and $R_2$ is alkyl containing 1–7 carbon atoms, such as n-butylamine, isobutylamine, sec.-butylamine, tert-butylamine, n-amylamine, or di-n-amylamine, or wherein
$R_1$ is hydrogen and $R_2$ is cycloalkyl or cycloalkylalkyl containing 3–7 carbon atoms such as cyclohexylamine, or wherein
$R_1$ is hydrogen and $R_2$ is an unsubstituted benzyl- or phenethyl group or a benzyl- or phenethyl group which is substituted by lower alkyl or methoxy, such as benzylamine, homoveratrylamine, or 3,4-dimethoxyphenethylamine, or wherein
$R_1$ and $R_2$ together form a straight or branched alkylene group containing 3–7 carbon atoms such as piperidine or 2-methylpiperidine; and
diamines of formula II wherein $R_3$, $R_4$, $R_5$, and $R_6$ are methyl such as tetramethylethylene diamine.

According to the present invention, there is further provided a biochemical reagent comprising a solution of an above-described amphipathic amine, preferably an amine of the above-defined especially preferred group of amphipathic amines of formula I or II, most preferably an amine of formula (I), wherein $R_1$ preferably is hydrogen and $R_2$ preferably contains 3 to 7 carbon atoms and represents alkyl, cycloalkyl or cycloalkylalkyl, in an aqueous physiological buffer solution. The solution is preferably buffered to a pH of about 7 to about 8 and/or is an isotonic solution. Examples of suitable buffer solutions are Tyrode's solution, isotonic tris (hydroxymethyl) amino methane buffer solution or phosphate buffer solutions or the like. The amount of amine may vary between 1 and about 500λ (1λ = $10^{-6}$ liters) per ml, preferably between 1 and 50 λ/ml.

According to the present invention, there is further provided a topical contraceptive composition, that is a composition which is adapted for application to the vaginal cavity of a female mammal, comprising a non-toxic and spermacidally effective amount of an above-described amphipathic amine per single dosage unit and a physiologically acceptable carrier.

It is well known in the medical art, that only such carrier compositions which exhibit a pH-value in the range of the vaginal pH (=pH 4.5–5), that is a slightly acidic carrier composition, are physiologically acceptable. In such a physiologically acceptable carrier the amphipathic amines naturally are present in salt-form. The amines may be incorporated into the composition in form of a free base, which will then form a salt with acidic components of the carrier, or in form of an acid-addition-salt with a pharmaceutically acceptable acid, e.g., a mineral acid such as hydrochloric acid or an organic acid such as citric acid. Preferred are such amines which are low in toxicity and low in skin-irritating side effects and preferably exhibit a high spermacidal activity. Especially suited are such amines of the above-defined especially preferred group of amphipathic amines of formulae I and II, preferably primary amines of formula I, wherein $R_2$ is a preferably primary alkyl group containing 3–7 carbon atoms, or a cycloalkyl- or cycloalkylalkyl group containing 3–7 carbon atoms, e.g., n-butylamine, cyclohexylamine and the like. The contraceptive composition may further comprise other conventional contraceptive agents and/or additives.

There is further provided according to the present invention a method for contraception which comprises applying the above-described topical contraceptive composition to the vaginal cavity of a female mammal.

Further objects, features and advantages of the present invention will become apparent from the detailed description of the invention and its preferred embodiments which follows.

DETAILED DESCRIPTION OF THE PREFERRED EMBODIMENTS

It has been found that the amphipathic amines according to the present invention exhibit valuable spermicidal properties and therefore are useful in biochemical research as agents for killing spermatozoa, especially for head/tail cleavage in mammalian spermatozoa, as well as in medical treatment as contraceptive agents for preventing pregnancy in female mammals.

In in vitro tests the compounds exhibit spermacidal activities at concentrations of from about 1 to 800 lambda per ml., preferably between 1 and 80 λ ml, as is indicated in the following tests evaluating their effects on sperm-motility and on sperm membrane character.

1. Motility and head membrane character: Ejaculates containing motile spermatozoa are centrifuged to remove seminal plasma components and resuspended in a physiological buffer, such as Tyrode's solution (pH=7.4). Sperm-concentrations are diluted to $10^7$ sperm/ml and the amine under test is added or conversely concentrated sperm-suspensions are added to buffered solutions already containing the amine. All tests have been carried out at 26° to 37° C. The motility and the morphological character of the membranes overlying the acrosomal region of the mammalian sperm head are accessed at intervals by phase-contrast microscopy. Percent motility and the percent of spermatozoa which have altered membranes over the head—seen as a lifting of an acrosomal cap or as a change in optical properties (refractive index) of the sperm head—are determined.

The following amines have been tested in Tyrode's solution:

n-butylamine, cyclohexylamine, benzylamine, di-n-amylamine, n-amylamine, tetramethylethylenediamine, 2-methylpiperidine, and homoveratrylamine.

In all tests, sperm-motility in the buffered solution is completely prevented at an amine concentration of 0.2 to 0.5% (w/v).

2. Detachment of sperm heads from their tails: Tests of the ability of these amines to detach the sperm tail from the base of the sperm head are conducted as follows. Seminal plasma-free spermatozoa are resuspended in tris buffer, pH 7.5, containing 0.9% NaCl and 0.01 M EDTA. After addition of the amine, the mixture is mixed vigorously for 30 seconds with a vortex mixer. The extent (percentage) of head detachment is determined by microscopic counting with phase-contrast optics. In this test, 15 lambda of n-butylamine, isobutylamine or cyclohexylamine, added to one ml of the buffered mixture containing $10^7$ spermatozoa, cause 93–99% of the spermatozoa to dissociate under head tail separation, and pure head and tail fractions can be isolated from the mixture by sucrose density gradient centrifugation. However, tri-n-butyl amine has no effect on the spermatozoa.

Representative compounds of various groups of differently substituted primary and secondary amines defined within the scope of the present invention, namely representatives of alkylamines, substituted alkylamines, cycloalkylamines, arylalkylamines, substituted arylalkylamines, and amines wherein the amino group is part of a non-aromatic heterocyclus, have been tested in the in vitro tests described above. The test results show that in spite of their different substitution, all these amines exhibit spermacidal activity. These test data indicate that a broad group of primary and secondary amines as defined within the present invention, possess spermacidal properties.

From the results of the tests it is further apparent that the spermacidal activity of the primary and secondary amines is retained in reaction media of varying pH-value within a pH-range of between about 7.5 and about 4, including the pH-values which are found at the vagina, and therefore are physiologically acceptable and non-irritating to the vaginal mucosa.

For the above-mentioned uses, the applied amounts of compounds can vary considerably, depending on the type of compound, the type of spermatozoa and the reaction medium.

For biochemical analysis purposes, good results are usually obtained in aqueous reaction media containing between about 1 and about 500, in particular between about 5 and about 50 lambda per ml.

For topical contraceptive purposes, good results are usually obtained with topical dosages of between 5 and 500 mg/per application. For example, primary amines containing 3 to 7 carbon atoms or heterocyclic amines containing 5 to 6 carbon atoms are preferably used in amounts of about 5 to about 300 mg/per application.

Sperm-motility-inhibiting activity of amines in samples of fresh semen has been tested as follows:

Portions of 1 microliter of the amine in free base form are directly added to 0.5 ml samples of fresh human semen and fresh rabbit semen at 37° C. The following amines are tested:

n-butylamine, isobutylamine, sec-butylamine, t-butylamine, n-amylamine, benzylamine, 3,4-dimethoxyphenylethylamine, cyclohexylamine, 2-methylpiperidine, and tetramethylethylenediamine.

All these amines completely inhibit sperm-motility within 10 minutes (range 5 sec.–10 min.) when the final concentration is 3–4% (w/v), preferably 0.5–4% (w/v).

Sperm-motility-inhibiting activity of amines contained in a carrier composition having a pH-value of between 4 and 6 has been tested as follows:

A mixture of a n-butylamine citrate solution in citrate buffer solution and glycerol, and a mixture of an aqueous cyclohexylamine hydrochloride solution and a hydroxyethylcellulose gel each are added portionwise to samples of fresh rabbit semen at 37° C. Sperm-motility is completely prevented within a period of ten minutes at a final amine concentration of between 3–4% (w/v), usually 1–5% (w/v).

The conception-preventing activity of n-butylamine and cyclohexylamine contained in a physiologically acceptable carrier composition has been tested in vivo. For this purpose the following compositions are prepared:

a. Cyclohexylamine containing composition. An aqueous solution of cyclohexylamine hydrochloride is incorporated into a hydroxyethylcellulose gel (commercial product K-Y Jelly) to form gel compositions containing 5–10% (w/w) of cyclohexylamine hydrochloride.

b. n-Butylamine containing composition. A solution of n-butylamine citrate in a citrate buffer solution (pH 5) is mixed with glycerol to form a solution containing 5% (w/w) of n-butylamine citrate. The compositions are tested as follows:

Female rabbits are selected for behavioral estrous, i.e. lordosis and receptivity to a male. Three or 8 cc of each of the above compositions is placed into the anterior vagina, in the proximity of the cervix, using the techniques of Adams* for deep intravaginal artificial insemination. Control and experimental females are then mated twice in succession to a male of proven fertility. Twenty-four to 30 hours later, these females are sacrificed, their reproductive tracts are divided into compartments, vagina, uterus and oviducts, with hemostat clamps and the contents of these are flushed out with Tyrode's solution (a balanced salt solution with glucose) and examined with a phase-contrast light microscope.

*Adams, C. E. (1962) Artifical insemination in rodents In: The Semen of Animals and Artificial Insemination, (J. P. Maule, ed.), Chapter 18, pp. 316–330, Commonwealth Agriculture Bureau.

Mating in the rabbit induces ovulation 9–10 hours after coitus. Eggs are recovered from the oviducts of all females tested. These are scored for cleavage, i.e. division into two cells or blastomeres, as an index of fertilization. Unfertilized eggs appear as a single large cell 24 to 30 hours after mating or in some cases these fragment into several cells which have a dark granular appearance. The control females with carrier alone are fertile, i.e. fertilization of all eggs occurs and spermatozoa are present in their uteri and vaginas. Females with carrier plus the amine (butylamine or cyclohexylamine salts) are non-fertile, i.e. fertilization does not occur, with the exception of one female tested. In this rabbit, two-thirds of the eggs have cleaved, but their appearance (i.e. the optical properties of the egg cytoplasm and the presence of blastomeres of unequal size) indicates that fertilization of these may have been delayed and occurred during the end of the fertile life (of some 6 to 8 hours) of these eggs. The uterus and vagina of this female contains motile spermatozoa, whereas the uteri of all other experimental females are devoid of spermatozoa and only dead or non-motile spermatozoa are occasionally seen in their vaginas.

The vagina of all females tested are examined visually at autopsy and the contents of the posterior and anterior portions of the vagina are examined microscopically for any signs of bleeding, surface hemorrhage or of excessive sloughing or desquamation of the epithelium of the vagina. None of the females examined, controls or amine instilled females, show any sign of bleeding or surface hemorrhage. The numbers of desquamated cells in the vaginal contents varies considerably between females and there appears to be no correlation between the nature of the material instilled and the numbers of cells in vaginal flushes.

The results of the above in vivo tests indicate that the tested amines are effective in preventing conception, provided that the carrier is placed in proximity to the cervix and is retained at this site for sufficient time to kill all spermatozoa in the ejaculates. It is known that sufficient spermatozoa can enter the cervix within several minutes after mating to fertilize all eggs—this is true of both rabbits and women. This population is called the cervical reservoir population and it appears that the function of this type of contraceptive is to prevent the extablishment of this reservoir of spermatozoa in the cervix.

No irritating effect of the tested amines on the vagina is observed in the in vivo test. It is evident from these test results that the skin-irritating properties, which the free amines are known to possess, are eliminated if these amines are contained in a composition which exhibits a pH-value which is in the range of the vaginal pH.

According to a further feature of the present invention, there are provided topical contraceptive compositions containing at least one amphipathic amine, which in these compositions is present in form of a salt. The compositions may take the form of formulations having a semi-solid consistency such as vaginal creams, creams to coat diaphragms or condoms, jellies, foams, aerosols, or the like or solid compositions which melt at body-temperature or disintegrate on contact with moisture, such as vaginal suppositories or tablets, e.g., polyethylene glycol-or glycerine-based suppositories, gel-forming tablets or effervescent tablets, and suppositories which effervesce on contact with moisture, tampons or soluble material, e.g., alginate wool, or the like.

The topical contraceptive compositions contain a non-toxic amount of the above-described amphipathic amines per dosage unit which is effective to prevent the entry of any fertilizing sperms into the female cervix, but which is non-irritating to the vaginal mucosa. The concentration of the amphipathic amine within the contraceptive composition may vary considerably depending on which amine is used, as well as on the chemical and physical properties of the other ingredients of the composition. Usually, the amount of amphipathic amine is between about 0.1 and about 50%, preferably between about 0.5 and about 50%, especially between about 1 and about 25% in semi-solid compositions and between about 0.1 and about 15%, especially between about 0.2 and about 10% in solid compositions.

The topical contraceptive composition may comprise supplementary topical antiseptic and germicidal agents which are conventionally used in topical contraceptive compositions in addition to the amphipathic amine. Suitable supplementary contraceptive agents are, e.g., physiologically acceptable mono(alkylphenyl) ethers of polyethylene glycols wherein the alkyl group preferably contains between 1 and 10 carbon atoms and the polyethylene glycol preferably contains 2 to 12 ethyleneoxy units, such as nonoxynol 9, a p-nonylphenyl ether of a polyethylene glycol, mono(isooctylphenyl)ether of polyethylene glycol, mono(p-diisobutylphenyl)ether of polyethylene glycol and the like, or physiologically acceptable benzyldimethylalkylphenoxyethoxyethyl ammonium salts wherein the alkyl groups preferably contain 1 to 10 carbon atoms, or benzyldimethylalkyl ammonium salts wherein the alkyl groups preferably contain 8 to 18 carbon atoms, such as methylbenzethonium or benzethonium salts, e.g., chlorides, or benzalkonium chloride.

Within the topical contraceptive formulation according to the present invention, the active ingredients are incorporated into water-soluble or water-dispersible conventional pharmaceutical carriers. Preferred are water-containing semi-solid formulations such as jellies, creams and foams. Jellies usually comprise an aqueous vehicle and a gel-forming and thickening agent. Preferred gel-forming agents are cellulose derivatives, e.g., cellulose ethers, especially cellulose lower alkyl ethers, such as methyl- or ethyl-cellulose or carboxymethylcellulose. Suitable water-soluble cellulose ethers may contain between 150 to 1,000 glucose units and may have a molecular weight between 40,000 and 190,000. Other gel-forming and thickening agents are vegetable gums which are stable at pH values between 4 and 9, preferably tragacanth or acacia, or physiologically acceptable synthetic thickening agents like polyvinyl alcohols, etc.

Suitable jelly-formulations comprise gels containing a cellulose-derivative such as hydroxyethylcellulose, and optionally adjuvants such as thickening agents, e.g., soluble starch, and moistening agents, e.g., propylene glycol, into which an amount of between about 5 to about 10% by weight of an acid-addition salt of the amine is incorporated.

Suitable cream-formulations may be in the form of water-in-oil or oil-in-water emulsions. The emulsion may contain oils which are commonly used in pharmaceutical compositions, e.g., vegetable oils, such as peanut oil or olive oil, or fatty acids, fatty alcohols and esters thereof. These creams may further contain conventional emulsifying agents, such as monoglycerides, alginates, fatty acid esters of sorbitane (spans) or ethoxylated derivatives thereof (tweens) and/or thickening agents. Foams and aerosols additionally contain physiologically acceptable conventional propelling agents, such as chlorofluoromethanes or -ethanes, e.g., $CFCl_3$ or $CF_2Cl_2$. Additional adjuvants which may be incorporated into these formulations are hygroscopic agents, such as glycerine or propylene glycol, physiologically acceptable buffer compositions, e.g., phosphate buffers, anti-molding agents, such as p-hydroxybenzoic acid lower alkyl esters, e.g., methylparaben or propylparaben, or sorbic acid, antiseptic agents, such as boric acid, cresols, chlorinated phenols, or organomercuric salts, e.g., phenylmercuric acetate, antioxidants, perfumes, etc.. Solid vaginal tablets may contain solid gel-forming carriers, e.g., the above-mentioned gel-forming agents, other water-soluble and/or hygroscopic conventional pharmaceutical solid carriers like sorbit, lactose, or polyvinylpyrrolidone, and may also comprise the above-mentioned adjuvants and conventional tabletting-adjuvants such as binders or lubricants. Suppositories may contain polyethylene glycols which are solid at normal temperatures, e.g., mixtures of polyethylene glycol 6000 (15 to 40%), polyethylene glycol 1540 (9 to 26%) and polyethylene glycol 400 (6 to 18%), carbowaxes, and glycerine, optionally in admixture with pharmaceutically acceptable fats and emulsifying agents and the above-mentioned adjuvants. Vaginal suppositories may also be in the form of soft gelatin capsules containing a liquid or semi-liquid water-soluble carrier material such as carboxymethylcellulose gels and glycerin into which an amount of from about 5 to about 10% by weight of a salt of the amine are incorporated. Preferably, the compositions are buffered to vaginal pH-values, that is, to a pH-value between about 4.5 and about 5, but higher pH-values up to about 7.5 are also acceptable. Effervescent suppositories or tablets further contain ingredients which will release an inert gas upon contact with moisture, e.g., mixtures of $NaHCO_3$ and $Na_2HPO_4$, which will form $CO_2$.

In order to yet further illustrate the objects and advantages of the present invention, the following examples will be given as illustrative, and not limitative.

EXAMPLE 1

Dissociation of mammalian sperms into heads and tails.

The heads of human, rabbit and mouse spermatozoa rapidly dissociate from their tails in the presence of primary amines.

In a typical experiment, 15 lambda of n-butylamine are added to $10^7$ spermatozoa in 1 ml of 0.1 M Tris, pH 7.2, +0.9% NaCl+5 mM EDTA; the mixture is immediately vortexed for 30 seconds and counted under phase-contrast optics for head-tail separation. Between 93 to 99% of spermatozoa dissociate under these conditions and pure head and tail fractions can be isolated by sucrose density gradient centrifugation. Electron microscopy of amine-treated rabbit spermatozoa reveals that head-tail separation occurs between the outer nuclear membrane and the basal plate of the tail-connecting piece, and between the inner and outer nuclear membranes at the tail implantation fossa. Isolated tails have intact connecting piece complexes with basal plates attached to the capitulum of the connecting piece.

The above experiment is repeated, but replacing the n-butylamine by other agents:

Whereas butanol and n-butylacetamide have no effect on spermatozoa, and tri-n-butylamine does not induce head-tail separation, the following amines have essentially the same activity as n-butylamine: cyclohexylamine, isobutylamine.

EXAMPLE 2

Comtraceptive jellies

| Compositions | 2A | 2B | 2C |
|---|---|---|---|
| Deionized water & buffer solution | 81.0% | 77.5% | 84.5% |
| Sodium carboxymethyl cellulose | 3.8% | — | — |
| Methyl cellulose | — | 3.5% | 3.5% |
| Glycerine | 5.0% | — | — |
| Propylene glycol | — | 3.0% | 3.0% |
| Methalparaben | 0.2% | 0.2% | 0.1% |
| Sodium borate | — | — | 2.9% |
| n-butylamine hydrochloride | 10.0% | 8.0% | 5.0% |
| Nonoxynol 9 | — | 7.8% | 0.8% |

| Compositions | 2A | 2B | 2C |
|---|---|---|---|
| Benzethonium chloride | — | — | 0.2% |

The water-soluble ingredients are dissolved in about 90% of the water, the pH of the solution is adjusted to 4.5 for compositions 2A and 2B and to 7.2 for composition 2C, the remaining water is added, then the gel-forming agent is added, and the mixture is allowed to convert into a gel.

The resulting jellies are filled into 100 g tubes provided with a measured dose-applicator for 1 ml per dose.

EXAMPLE 3

Contraceptive Cream 30 parts per weight of n-butylamine are incorporated into 70 parts per weight of an oil-in-water emulsion containing water glycerine, tragacanth glycerinemonostearate, stearic acid, peanut oil and cetyl alcohol.

The resulting cream is filled into 100 g tubes provided with a measured dose-applicator for 1 ml per dose.

EXAMPLE 4

Contraceptive Suppositories 20 parts per weight of cyclohexylamine* are incorporated into 80 parts per weight of a molten water-miscible suppository-base containing 5% glycerine and polyethylene glycols. The warm liquid is filled into 500 mg suppository-molds and allowed to cool.

*in the form of its citrate

While the invention has now been described in terms of various preferred embodiments, and exemplified with respect thereto, the skilled artisan will readily appreciate that various modifications, changes, substitutions, and omissions may be made without departing from the spirit thereof. Accordingly, it is intended that the present invention be limited solely by the scope of the following claims.

What is claimed is:

1. A method for killing mammalian spermatozoa, which comprises contacting spermatozoa with a spermicidally effective amount of an amphipathic organic amine of the formula (I)

wherein $R_1$ represents hydrogen, and $R_2$ represents an alkyl-, cycloalkyl- or cycloalkylalkyl-group containing 3 to 7 carbon atoms.

2. The method as defined in claim 1, wherein $R_2$ represents a primary alkyl group.

3. The method as defined in claim 1, wherein $R_2$ represents n-butyl.

4. The method as defined in claim 1, wherein $R_2$ represents isobutyl.

5. The method as defined in claim 1, wherein $R_2$ represents cyclohexyl.

6. A method for preventing pregnancy which comprises the step of applying to the vaginal cavity of a mammalian female an amount of a topical contraceptive composition having a semi-solid or solid consistency, exhibiting a pH-value of between about 4.5 and about 7.5 and comprising a non-toxic conception-inhibiting amount of an aphipathic amine as defined in claim 1 per single dosage unit and a physiologically acceptable carrier, said amount being sufficient to prevent the entry of fertilizing sperms into the female cervix.

7. The method as defined in claim 6, wherein the amount of the topical contraceptive composition comprises about 5 to about 500 mg of the amine.

8. The method as defined in claim 7, wherein the amount of the topical contraceptive formulation comprises about 5 to about 300 mg of the amine.

9. A method as defined by claim 6, wherein $R_2$ represents n-butyl.

10. A method as defined by claim 6, wherein $R_2$ represents isobutyl.

11. A method as defined by claim 6, wherein $R_2$ represents cyclohexyl.

* * * * *